(12) United States Patent
Jain

(10) Patent No.: US 9,675,304 B2
(45) Date of Patent: Jun. 13, 2017

(54) LIVE 3D ANGIOGRAM USING REGISTRATION OF A SURGICAL TOOL CURVE TO AN X-RAY IMAGE

(75) Inventor: Ameet Kumar Jain, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 191 days.

(21) Appl. No.: 14/127,673

(22) PCT Filed: Jun. 7, 2012

(86) PCT No.: PCT/IB2012/052877
§ 371 (c)(1),
(2), (4) Date: Dec. 19, 2013

(87) PCT Pub. No.: WO2013/001388
PCT Pub. Date: Jan. 3, 2013

(65) Prior Publication Data
US 2014/0114180 A1    Apr. 24, 2014

Related U.S. Application Data

(60) Provisional application No. 61/501,279, filed on Jun. 27, 2011.

(51) Int. Cl.
*A61B 5/05* (2006.01)
*A61B 6/12* (2006.01)
*A61B 6/00* (2006.01)
*A61B 34/20* (2016.01)
*A61B 90/00* (2016.01)

(52) U.S. Cl.
CPC ............... *A61B 6/12* (2013.01); *A61B 6/466* (2013.01); *A61B 6/481* (2013.01); *A61B 6/504* (2013.01); *A61B 6/507* (2013.01); *A61B 34/20* (2016.02); *A61B 2034/2061* (2016.02); *A61B 2090/364* (2016.02); *A61B 2090/376* (2016.02)

(58) Field of Classification Search
CPC ....... A61B 5/06; A61B 5/6858; A61B 6/4441; A61B 6/487
See application file for complete search history.

(56) References Cited

U.S. PATENT DOCUMENTS

| 7,840,252 B2 | 11/2010 | Strommer |
| 8,050,739 B2 | 11/2011 | Eck et al. |
| 8,108,029 B2 | 1/2012 | Rasche |

(Continued)

FOREIGN PATENT DOCUMENTS

EP    2187353 A2    5/2010

OTHER PUBLICATIONS

Martin Glockner: "Catheterization in Congenital Heart Disease with Syngo iPilot", AXIOM Innovations, Jun. 1, 2011 (Jun. 1, 2011), pp. 30-33, XP002686314.

(Continued)

*Primary Examiner* — Joel Lamprecht

(57) ABSTRACT

A method, system, and program product are provided for providing a live 3D image of a body lumen. The 3D shape of a flexible surgical tool in the body lumen is determined using optical shape sensing. An x-ray image is taken of the body lumen, with at least one of the body lumen and the surgical tool being radiopaque. The determined 3D surgical tool shape is registered to the x-ray image.

15 Claims, 3 Drawing Sheets

(56) References Cited

U.S. PATENT DOCUMENTS 8,494,245 B2 * 7/2013 Liao .................... A61B 6/4441
345/419
2006/0064006 A1 * 3/2006 Strommer et al. ............ 600/415
2010/0030063 A1 2/2010 Lee

OTHER PUBLICATIONS

Jain Ameet et al., "3D TEE Registration with X-Ray Fluoroscopy for Interventional Cardiac Applications", 5th International Conference on Functional Imaging and Modeling of the Heart, Proceedings, Lecture Notes in Computer Science, vol. 5528 pp: 321-329, Jun. 2009.

Gao G. et al., "Rapid Image Registration of Three-Dimensional Transesophageal Echocardiography and X-Ray Fluoroscopy for the Guidance of Cardiac Interventions", 1st International Conference on Information Processing in Computer-Assisted Interventions (IPCAI 2010) Geneva, Switzerland, Jun. 23, 2010, Lecture Notes in Computer Science, vol. 6135 pp. 124-134.

* cited by examiner

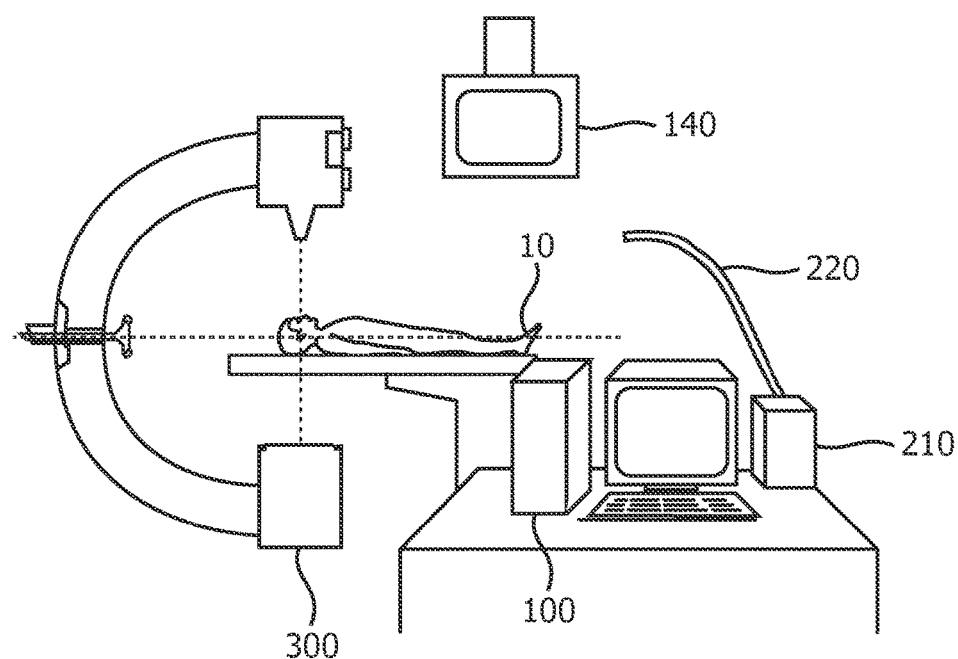
FIG. 1
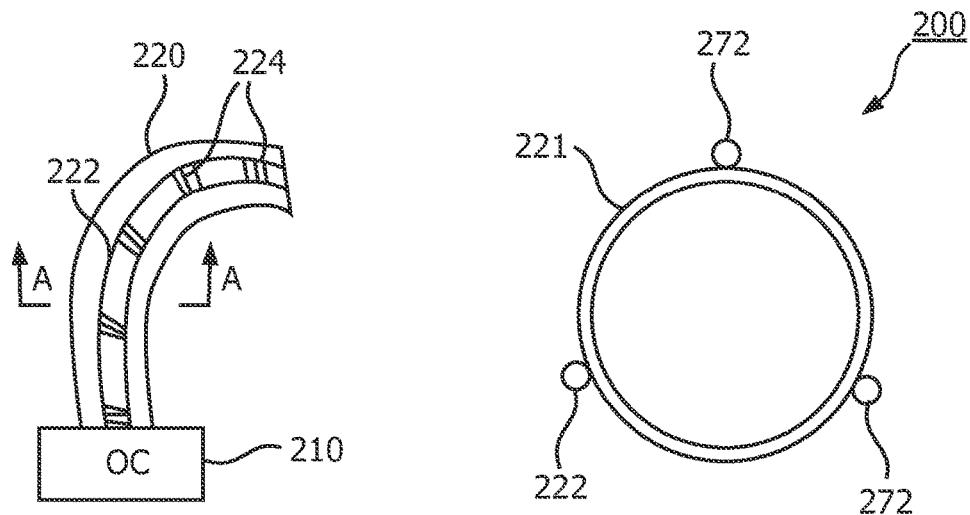
FIG. 2
FIG. 3

LIVE 3D ANGIOGRAM USING REGISTRATION OF A SURGICAL TOOL CURVE TO AN X-RAY IMAGE

CROSS-REFERENCE TO PRIOR APPLICATIONS

This application is the U.S. National Phase application under 35 U.S.C. §371 of International Application Serial No. PCT/IB2012/052877, filed on Jun. 7, 2012, which claims the priority benefit under 35 U.S.C. §119(e) of U.S. Provisional Application No. 61/501,279 filed on Jun. 27, 2011, the contents of which are herein incorporated by reference.

FIELD OF THE INVENTION

The invention relates to the field of medical imaging and more particularly to a method and system for providing a live angiogram using registration of a surgical tool curve to an x-ray image during an intervention.

BACKGROUND

Simultaneous tool tracking and vessel reconstruction in cardiac intervention is a significant challenge. One known approach is to use electromagnetic (EM) tracking of a catheter tip and overlay the detected position of the catheter tip onto a 3D image reconstruction from a previously performed CT scan. However, this approach provides limited accuracy, due, at least partially, to motion from bodily functions such as breathing and the beating of the patient's heart. Also, the CT scan is not performed in real-time due to the time required for the procedure. Another known approach is to perform a rotational cone-beam scan using a CT scanner and calculate the catheter shape from the multiple 2D projections on the x-rays. This approach requires multiple x-rays and corresponding radiation doses, and also suffers from the problem of movement between poses.

Angiograms are a real-time modality for observing and measuring structural and functional characteristics of a patient's coronary system for use in diagnostic and corrective procedures. Currently, to perform a 3D angiogram, a contrast catheter is positioned in a vessel at an area of interest, an x-ray image is taken at a first angle, the x-ray machine is repositioned to a second angle, a second x-ray image is taken at the second angle, and a 3D image is reconstructed from the x-ray images. However, this method suffers from movement between images due to breathing and heart beating. Moreover, multiple x-rays expose the patient and medical personnel to increase doses of radiation.

SUMMARY

The present invention provides a method, system and program product for providing a live 3D angiogram using registration of a surgical tool curve to an x-ray image. The shape of the surgical tool is determined by optical shape sensing (OSS) in which at least one longitudinal optical fiber with a plurality or continuum of optical sensors or sensing comprising optical fiber cores with scattering sources such as Fiber Bragg Gratings or Rayleigh scatterers disposed in the tool that shift the reflected light wavelength in response to the local strain in the fiber. OSS is understood to include fiber optics for shape sensing or localization generally, including, for example, sensing or localization from detection of variation in one or more sections in a fiber using back scattering, optical fiber force sensing, fiber location sensors, Fiber Bragg Gratings or Rayleigh scattering. An optical console interrogates the sensors and detects reflected light. A processor calculates local curvature along the lengths of the sensors from the shift in reflected wavelength to determine the three-dimensional shape of the tool. An x-ray image is taken of the area where the tool is located, and the 3D tool shape is registered to the 2D segmented image. A 3D rendering is made from the 2D image and the 3D shape.

According to one embodiment, a method is provided for providing a live 3D image of a body lumen. The method comprises determining the 3D shape of a flexible surgical tool in the body lumen using optical shape sensing. An x-ray image of the body lumen is taken, with at least one of the body lumen and the surgical tool being radiopaque. The determined 3D surgical tool shape is registered to the x-ray image.

In one embodiment the registering step comprises: segmenting a 2D image of the tool in the x-ray image, and recovering a pose of the 2D x-ray image of the tool. The segmentation may be performed using any suitable technique to provide a set of coordinate pairs corresponding to the tool. Pose recovery may be performed with any suitable method, such as iterative closed point (ICP), the Rosenhahn approach, or the like.

According to one embodiment of the present invention, the method may further comprise: calculating the 3D tool shape in x-ray space; and super-posing features from the x-ray image onto the determined 3D shape. The 3D tool shape may then be displayed on a display with x-ray features super-posed thereon.

According to one embodiment, the tool is a contrast catheter, and the step of taking an x-ray image comprises delivering contrast dye through the catheter to make the catheter radiopaque.

According to one embodiment, the body lumen is at least one blood vessel. The 3D tool shape displayed with x-ray features super-posed thereon may be an angiogram.

According to one embodiment, the step of taking an x-ray image is repeated, the 3D tool shape is determined in real time, and the 3D tool shape with x-ray features super-posed thereon is displayed in real time.

According to one embodiment a system is provided for providing a live 3D image of a body lumen. The system comprises a surgical tool having attached thereto, at least one optic fiber with shape sensing sensors formed therein. At least one processor is also provided. An optics module is operably connected to the at least one processor, and comprising a light source. An x-ray system is operably connected to the at least one processor. At least one memory is also operably connected to the at least one processor. At least one program of instruction is encoded on the at least one memory, the at least one program of instruction executable by the at least one processor to: interrogate the shape sensors using the light source in the optics module and determine the 3D shape of a flexible surgical tool in the body lumen using optical shape sensing; take an x-ray image of the body lumen, at least one of said body lumen and said surgical tool being radiopaque; and register the determined 3D surgical tool shape to the x-ray image.

According to one embodiment the above described system further comprises a display, and the at least one program of instruction further comprises, program instructions encoded on the at least one memory to display the 3D tool shape on the display.

According to one embodiment, the program instructions for registering the determined 3D tool shape comprise program instructions encoded on the at least one memory to:

segment a 2D image of the tool in the x-ray image; and recover a pose of the 2D x-ray image of the tool.

According to one embodiment, the program instructions further comprise program instructions encoded on the at least one memory to: calculate the 3D tool shape in x-ray space, and super-pose features from the x-ray image onto the determined 3D shape In one embodiment, the tool is a contrast catheter, that delivers contrast dye through the catheter prior to taking an x-ray image to make the catheter radiopaque.

According to one embodiment a computer program product is provided comprising a tangible, computer-readable storage device having a program of instructions encoded thereon, comprising: program instructions for determining the 3D shape of a flexible surgical tool in the body lumen using optical shape sensing; program instructions for taking an x-ray image of the body lumen, at least one of said body lumen and said surgical tool being radiopaque; and program instructions for registering the determined 3D surgical tool shape to the x-ray image.

According to one embodiment, the program instructions for registering the determined 3D surgical tool shape comprise: program instructions for segmenting a 2D image of the tool in the x-ray image, and program instructions for recovering a pose of the 2D x-ray image of the tool.

According to one embodiment, the computer program product further comprises: program instructions encoded on the tangible, computer-readable storage device for calculating the 3D tool shape in x-ray space, and program instructions encoded on the tangible, computer-readable storage device for super-posing features from the x-ray image onto the determined 3D shape.

According to one embodiment the computer program product further comprises: program instructions encoded on the tangible, computer-readable storage device for displaying the 3D tool shape with x-ray features super-posed thereon.

According to one embodiment, the program instructions for taking an x-ray image are repeated, and the computer program product further comprises: program instructions encoded on the tangible, computer-readable storage device for determining the 3D tool shape in real time, and program instructions encoded on the tangible, computer-readable storage device for displaying the 3D tool shape with x-ray features super-posed thereon in real time.

BRIEF DESCRIPTION OF THE DRAWINGS

The features and advantages of the invention will be more clearly understood from the following detailed description of the preferred embodiments when read in connection with the accompanying drawing. Included in the drawing are the following figures:

FIG. 1 is an isometric view of an imaging system used in an embodiment of the present invention;

FIG. 2 is a side view of a surgical tool configured for optical shape sensing for use in providing a live 3D angiogram using registration of the surgical tool's curve to an x-ray image according to an embodiment of the present invention;

FIG. 3 is a sectional view of the surgical tool of FIG. 2 taken at line A-A;

DETAILED DESCRIPTION

Figure 4:
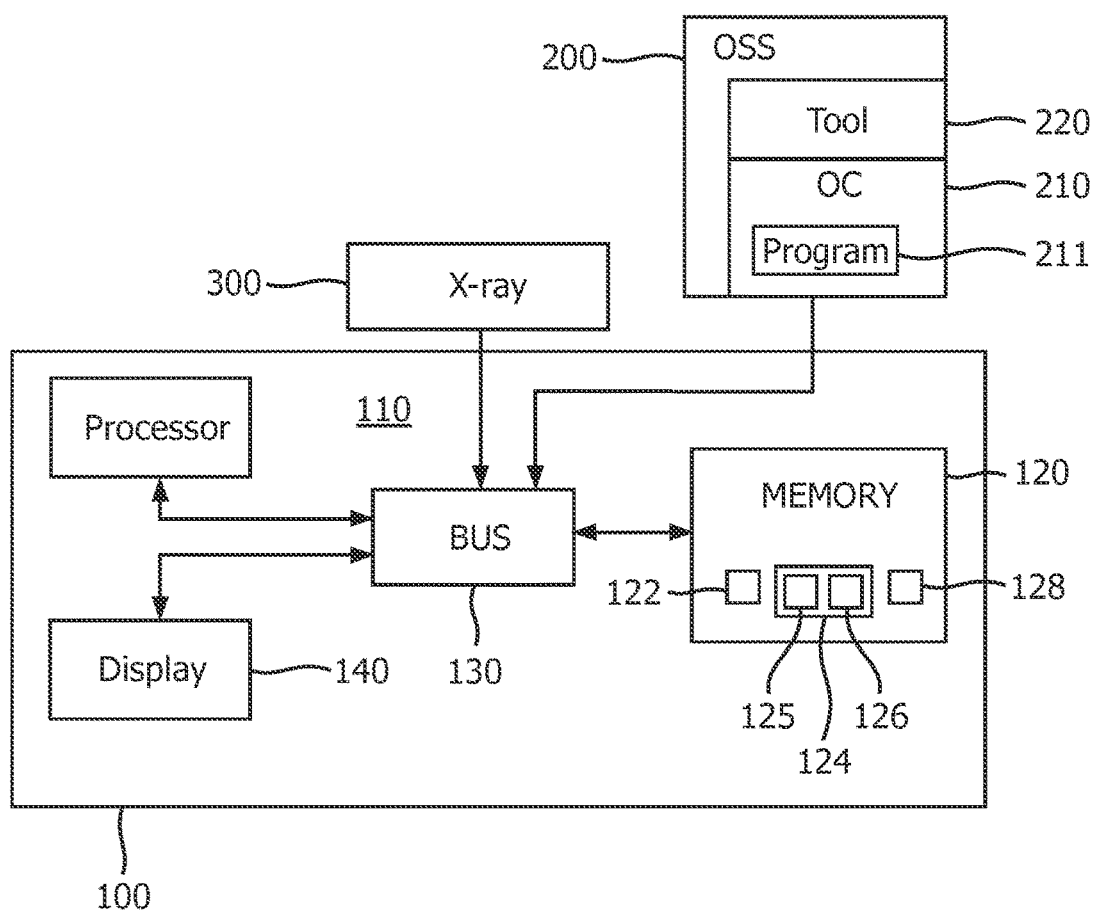
FIG. 4 is a block diagram of a system for live 3D angiogram using registration of a surgical tool curve to an x-ray image according to an embodiment of the present invention.

The present invention provides a method, system and program product for providing a live 3D angiogram using registration of a surgical tool curve to an x-ray image.

FIG. 1 shows an imaging system used for providing a live 3D angiogram using registration of a surgical tool curve to an x-ray image according to an embodiment of the present invention. The imaging system comprises an x-ray machine 300 disposed for taking x-ray imagers of a patient on a table 10. A processing system 100, such as a general purpose computer is operably connected to the x-ray machine and processes x-ray images from the x-ray machine 300. The processed image may be presented on a display 140.

A flexible surgical tool 220 is configured for Optical Shape Sensing (OSS). According to one embodiment, the shape of the surgical tool 220 is determined by optical shape sensing (OSS) in which at least one longitudinal optical fiber 222, as shown in FIGS. 2 and 3, is fitted with a plurality of optical sensors 224 comprising optical fiber cores with scattering sources such as Fiber Bragg Gratings or Rayleigh scatterers disposed in the tool that shift the reflected light wavelength in response to the local strain in the grating. An optical console 210 interrogates the sensors 224 and detects reflected light.

According to one embodiment, the surgical tool 220 is a contrast catheter 221. The contrast catheter is a flexible hollow tube which conforms to the shape of a blood vessel and delivers contrast dye, through its hollow opening to an area of interest so that it can be seen on an x-ray image. Contrast catheters may be used to visualize blood vessels, such as for detection of blockage and aneurysms, and to determine blood flow by the movement or dissipation of the contrast dye over time, as well as observing other structural and functional characteristics.

At least one optic fiber 222 is fixed to the catheter 221 in a longitudinal direction. The optic fiber(s) may be affixed to the outside wall of the catheter by adhesive, sewing, or any other suitable attachment technique. Alternatively, the optic fiber(s) may be fixed inside the catheter or into the wall itself using any suitable technique. While one optic fiber 222 may be used, a plurality of fibers may be used instead, and may be at uniform, radial spacing, as shown in FIG. 3.

The optical console 210 may comprise a processor 211 for controlling the interrogation of the sensors 224 and for calculating the local curvature at each sensor 224 in 3D space from the shift in the reflected wavelength of the reflected light at time intervals corresponding to the locations of the sensors 224. The processor 211 may also calculate the 3D shape of the surgical tool 220 from the local curvatures. Alternatively, one or more of the interrogation control and the calculations may be performed by the processor 110 in the processing system 100. The 3D shape may be stored as a set of 3 coordinate (x,y,z) triples.

A system for providing a live 3D angiogram using registration of a surgical tool curve to an x-ray image according to an embodiment of the present invention is shown in FIG. 4. The system comprises a processor 110, a memory 120, a display 140, an x-ray system 300, and an optical shape sensing system 200.

The processor 110 is operably connected to the memory 120. According to one embodiment, they are connected through a bus 130. The processor 110 may be may be any device capable of executing program instructions, such as one or more microprocessors. The memory may be any volatile or non-volatile memory device, such as a removable disc, a hard drive, a CD, a Random Access Memory (RAM), a Read Only Memory (ROM), or the like. Moreover, the processor 110 may be embodied in a general purpose computer.

A display 140 is also operably connected to the processor 110. The display may be any monitor, screen, or the like suitable for presenting a graphical user interface (GUI) capable of presenting medical images.

An x-ray system 300 is operably connected to the processor 110. The x-ray system provides x-ray imaging data to the processor 110 for processing to create an x-ray image of anatomical features. The x-ray image is then presented on the display 140.

The memory 120 has encoded thereon, program instructions 122 which are executable by the processor 110 to process x-ray images from the x-ray system 300. In addition to the program instructions 122 for processing the x-ray image for presentation on display 140, a program of instruction 124 is also provided that performs registration of 2D x-ray images to a 3D image space of the tool 220 shape.

The registration program of instruction 124 comprises segmentation program instructions 125 executable by the processor 10 to locate the blood vessel or surgical tool 220 with contrast dye therein within the 2D x-ray image using segmentation. That is, the location program instructions 125 locate the position of the blood vessel or tool 220 (which conforms to the blood vessel) within the 2D x-ray image frame. The location or segmentation program instructions 125 may use any segmentation program suitable for locating the center of a high contrast image segment within an x-ray image. These segmentation programs are well know in the art and will not be described further in this application. The location program instructions 125 may be a part of a registration program 124, or may be a separate program or module callable by the registration program 124.

The registration program of instructions 124 further comprises pose recovery program instructions 126 executable by the processor 110 to recover the pose of the 3D tool shape relative to the x-ray source. The pose may be represented by a matrix to resolve the six degrees of freedom of the tool (3 translations: in x, y, and z directions, and 3 rotations: about the x, y, and z axes). With a known 3D shape and a known 2D projection of that shape, the pose recovery matrix can be calculated using any of a plurality of known methods, such as the Rosenhahn method, the iterative closed point (ICP) method, or a combination of the ICP method with the Procrustes method.

The registration program of instructions 124 then calculates the 3D curve in x-ray space using the pose recovery matrix to register the 3D shape to the 2D x-ray space. That is, each voxel of shape on the 2D x-ray image can be converted to a 3 coordinate location using the pose recovery matrix.

According to one embodiment, a correspondence program of instruction 128 is also encoded on memory 120. The correspondence program of instruction 128 is executed by the processor 110 to super-pose features from the 2D x-ray image onto a 3D representation of the tool/blood vessel shape, using the recovery matrix. The correspondence program may be stored on the same memory as the registration program or a different memory. Also, the correspondence program of instruction 128 may be a part of the registration program of instruction 124.

The correspondence program of instruction 128 further includes instructions that are executed by the processor 110 to display the 3D tool shape with super-posed features on the display 140.

Figure 5:
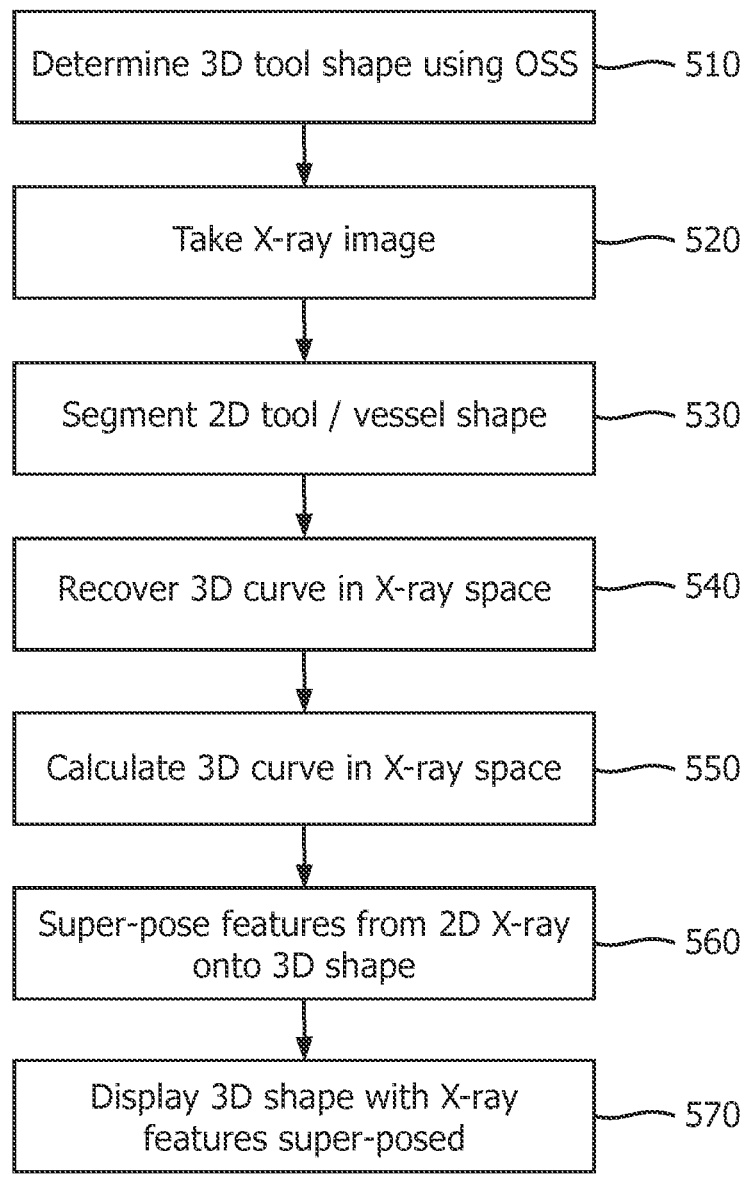
FIG. 5 is a block diagram of a method for live 3D angiogram using registration of a surgical tool curve to an x-ray image according to an embodiment of the present invention.

FIG. 5 is a block diagram of a method for live 3D angiogram using registration of a surgical tool curve to an x-ray image according to an embodiment of the present invention. While the following description discusses a procedure in the blood vessels, it should be understood that this invention is not limited to this example. Rather the invention may be practiced during a procedure in any body lumen. Moreover, while the following description discusses a catheter, it should be understood that other surgical tools could also be used, as long as the tool conforms to the shape of the body lumen.

A physician advances a contrast catheter 221 with optical shape sensing sensors 224 affixed thereto to an area of interest in a patient's blood vessel. The catheter 221 conforms to the shape of the blood vessel. The OSS system 200 determines the shape of the catheter 221, which is also the shape of the blood vessel in which the catheter is located (Step 510).

The physician injects contrast dye through the catheter 221 to render the catheter (or blood vessel) radiopaque so that it will be visible on an x-ray image, and takes an x-ray image showing the catheter 221 (or blood vessel) (Step 520). In an alternative embodiment, the catheter, or another surgical tool is itself radiopaque and no contrast dye is required.

The processor 110, segments the catheter 221 (or blood vessel) in the x-ray image using the segmentation program of instruction 125 (Step 530) to locate the blood vessel in 2D x-ray space and determine the 2D shape of the catheter 221. That is, the 2D projection of the catheter on the plane of the x-ray image. The 2D shape is stored as a plurality of (x,y) coordinate pairs corresponding to voxels that comprise the shape in 2D x-ray space. Note that the segmentation program of instruction 125 will also determine and save local properties of the catheter/blood vessel (e.g. thickness, brightness, etc.) that will be clinically interesting. For example, thickness can be used as a measure of blockage of the blood vessel.

The pose recovery program of instruction 126 recovers the pose of the catheter/blood vessel relative to the x-ray source (Step 540). That is, the pose recovery program of instruction 126 determines the recovery matrix (the 3 translations and 3 rotations that define the position (location and orientation) of the catheter/blood vessel in x-ray space.

The registration program of instructions 124 then calculates the 3D curve in x-ray space using the pose recovery matrix to register the 3D shape to the 2D x-ray space (Step 550). That is, each voxel of the tool shape on the 2D x-ray image can be converted to a 3 coordinate location using the pose recovery matrix (the third coordinate being the distance from the x-ray source) to reconstruct a 3D shape.

The correspondence program of instruction 128 is executed by the processor 110 to super-pose features from the 2D x-ray image onto a 3D representation of the tool/blood vessel shape, using the recovery matrix (Step 560). For example, the thickness of the tool/blood vessel may be calculated from the segmentation of the x-ray image and super-posed on the 3D representation of the tool/blood vessel. The correspondence program may be stored on the same memory as the registration program or a different memory. Also, the correspondence program of instruction 128 may be a part of the registration program of instruction 124.

The correspondence program of instruction 128 is executed by the processor 110 to display the 3D shape of the tool/blood vessel with features from the 2D x-ray superposed on it as a 3D angiogram (Step 570).

According to an embodiment of the present invention, two or more x-ray images are taken at the same pose at a predefined time interval. Both x-rays are registered to their respective 3D tool/blood vessel shapes, which are displaced relative to each other due to the beating of the patient's heart. Blood flow can be determined by measuring the movement of the contrast dye relative to the 3D toll/blood vessel shape.

According to another embodiment, multiple 3D angiograms may be stitched together to create a larger angiogram.

According to one embodiment, the 3D visualization of the toll/blood vessel may be used for real-time guidance of an intervention procedure.

The invention can take the form of program instructions encoded on a tangible medium. As such, the invention can be an entirely hardware embodiment or an embodiment containing both hardware and software elements. In an exemplary embodiment, the invention is implemented in software, which includes but is not limited to firmware, resident software, microcode, etc.

Furthermore, the invention may take the form of a non-volatile computer program product accessible from a computer-usable or computer-readable medium providing program code for use by or in connection with a computer or any instruction execution system or device. For the purposes of this description, a computer-usable or computer readable medium may be any apparatus that can contain or store the program for use by or in connection with the instruction execution system, apparatus, or device.

The foregoing method may be realized by a program product comprising a machine-readable medium having a machine-executable program of instructions, which when executed by a machine, such as a computer, performs the steps of the method. This program product may be stored on any of a variety of known machine-readable medium, including but not limited to compact discs, floppy discs, USB memory devices, and the like.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention. The scope of the invention is intended to encompass equivalent variations and configurations to the full extent of the following claims.

What is claimed is:

1. A method for providing a live 3D image of a body lumen, comprising the steps of:
    determining the 3D shape of a flexible surgical tool in the body lumen using optical shape sensing;
    taking an x-ray image of the body lumen, at least one of said body lumen and said surgical tool being radiopaque;
    segmenting a 2D projection of the tool in the x-ray image; and
    calculating a pose recovery matrix using the determined 3D shape and the segmented 2D projection.

2. The method of claim 1, further comprising:
    calculating the 3D tool shape in x-ray space; and
    super-posing features from the x-ray image onto the determined 3D shape.

3. The method of claim 2, further comprising:
    displaying the 3D tool shape with x-ray features superposed thereon.

4. The method of claim 3, wherein the tool is a contrast catheter, and the step of taking an x-ray image comprises delivering contrast dye through the catheter to make the catheter radiopaque.

5. The method of claim 4, wherein the body lumen is at least one blood vessel.

6. The method of claim 4, wherein the step of taking an x-ray image is repeated, the 3D tool shape is determined in real time, and the 3D tool shape with x-ray features superposed thereon is displayed in real time.

7. A system for providing a live 3D image of a body lumen, comprising:
    a surgical tool having attached thereto, at least one optic fiber with shape sensing sensors formed therein;
    at least one processor;
    an optics module operably connected to the at least one processor, and comprising a light source;
    an x-ray system operably connected to the at least one processor;
    at least one memory operably connected to the at least one processor; and
    at least one program of instruction encoded on the at least one memory, the at least one program of instruction executable by the at least one processor to:
    interrogate the shape sensors using the light source in the optics module and determine the 3D shape of a flexible surgical tool in the body lumen using optical shape sensing;
    take an x-ray image of the body lumen, at least one of said body lumen and said surgical tool being radiopaque; and
    segment a 2D projection of the tool in the x-ray image; and
    calculate a pose recovery matrix using the determined 3D shape and the segmented 2D projection.

8. The system of claim 7, further comprising a display, wherein the at least one program of instruction further comprises, program instructions encoded on the at least one memory to display the 3D tool shape on the display.

9. The system of claim 7, wherein the program instructions further comprise program instructions encoded on the at least one memory to:
    calculate the 3D tool shape in x-ray space; and
    super-pose features from the x-ray image onto the determined 3D shape.

10. The system of claim 9, wherein the tool is a contrast catheter, to deliver contrast dye through the catheter prior to taking an x-ray image to make the catheter radiopaque.

11. A computer program product comprising a tangible, computer-readable storage device having a program of instructions encoded thereon, comprising:
    program instructions for determining the 3D shape of a flexible surgical tool in the body lumen using optical shape sensing;
    program instructions for taking an x-ray image of the body lumen, at least one of said body lumen and said surgical tool being radiopaque;
    program instructions for segmenting a 2D projection of the tool in the x-ray image; and program instructions for calculating a pose recovery matrix using the determined 3D shape and the segmented 2D projection.

12. The computer program product of claim 11, further comprising:

program instructions encoded on the tangible, computer-readable storage device for calculating the 3D tool shape in x-ray space; and program instructions encoded on the tangible, computer-readable storage device for super-posing features from the x-ray image onto the determined 3D shape; and registering the determined 3D surgical tool shape to the x-ray image.

13. The computer program product of claim 12, further comprising:

program instructions encoded on the tangible, computer-readable storage device for displaying the 3D tool shape with x-ray features super-posed thereon.

14. The computer program product of claim 13, wherein the tool is a contrast catheter, and prior to taking an x-ray image, a contrast dye is delivered through the catheter to make the catheter radiopaque.

15. The computer program product of claim 13, wherein the program instructions for taking an x-ray image are repeated, and further comprising:

program instructions encoded on the tangible, computer-readable storage device for determining the 3D tool shape in real time; and program instructions encoded on the tangible, computer-readable storage device for displaying the 3D tool shape with x-ray features super-posed thereon in real time.

* * * * *